US011862318B2

(12) United States Patent
Crothall et al.

(10) Patent No.: US 11,862,318 B2
(45) Date of Patent: *Jan. 2, 2024

(54) NETWORK TOPOLOGY FOR INSULIN PUMP SYSTEMS

(71) Applicant: Insulet Corporation, Acton, MA (US)

(72) Inventors: George Crothall, Oceanside, CA (US); Yean W. Chan, Irvine, CA (US)

(73) Assignee: INSULET CORPORATION, Acton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/307,219

(22) Filed: Apr. 26, 2023

(65) Prior Publication Data
US 2023/0268048 A1 Aug. 24, 2023

Related U.S. Application Data

(60) Continuation of application No. 17/247,600, filed on Dec. 17, 2020, which is a division of application No.
(Continued)

(51) Int. Cl.
| | |
|---|---|
| *G16H 20/17* | (2018.01) |
| *A61B 5/145* | (2006.01) |
| *G16H 40/63* | (2018.01) |
| *G16H 40/67* | (2018.01) |
| *A61M 5/142* | (2006.01) |
| *H04W 52/02* | (2009.01) |
| *A61B 5/00* | (2006.01) |

(52) U.S. Cl.
CPC ......... *G16H 20/17* (2018.01); *A61B 5/14532* (2013.01); *A61M 5/14244* (2013.01); *G16H 40/63* (2018.01); *G16H 40/67* (2018.01); *H04W 52/0216* (2013.01); *A61B 5/74* (2013.01); *A61M 2205/3546* (2013.01); *Y02D 30/70* (2020.08)

(58) Field of Classification Search
CPC ........ A61M 5/142; A61B 5/1453; A61B 5/74; H04W 4/80; H04W 52/02; G16H 40/63; G16H 40/67
See application file for complete search history.

(56) References Cited

U.S. PATENT DOCUMENTS

2014/0379358 A1\* 12/2014 Chovanda .............. G16H 50/20
705/2

\* cited by examiner

*Primary Examiner* — Tiffany Legette
(74) *Attorney, Agent, or Firm* — GOODWIN PROCTER LLP

(57) ABSTRACT

In one implementation, an insulin delivery system using an on-body network includes an insulin delivery device that is adapted to administer dosages of insulin to a patient; a controller that is adapted to control operation of the insulin delivery device, to establish a first network connection in which the controller acts in a central role, and to establish a second network connection in which the controller acts in a peripheral role; one or more peripheral devices that are adapted to generate patient data related to blood glucose levels and to transmit the patient data wirelessly over the first network connection, the peripheral devices acting in a peripheral role over the first network connection; and a mobile application installed on a mobile computing device that is programmed to communicate with the controller over the second network connection, the mobile application communicating in a central role over the second network connection.

16 Claims, 4 Drawing Sheets

Related U.S. Application Data

15/688,271, filed on Aug. 28, 2017, now Pat. No. 10,896,245.

(60) Provisional application No. 62/380,864, filed on Aug. 29, 2016.

NETWORK TOPOLOGY FOR INSULIN PUMP SYSTEMS

CROSS-REFERENCE TO RELATED APPLICATIONS

This application is a continuation application of U.S. application Ser. No. 17/247,600, filed Dec. 17, 2020, which is a divisional of and claims priority to U.S. application Ser. No. 15/688,271, filed on Aug. 28, 2017, entitled, "Network Topology for Insulin Pump 5 Systems," which claims priority to U.S. Application Ser. No. 62/380,864, filed on Aug. 29, 2016, all of which are incorporated by reference in their entireties herein.

TECHNICAL FIELD

This document relates to network topology for insulin pump systems, such as systems including mobile computing devices (e.g., smartphones), insulin delivery devices (e.g., insulin pump devices), and peripheral devices (e.g., blood glucose meters (BGM), continuous glucose monitors (CGM)).

BACKGROUND

Insulin infusion pumps, continuous glucose monitors (CGM), and blood glucose meters (BGM) (and other medical equipment) are intended to be used for many consecutive years as part of insulin pump systems that deliver insulin at appropriate dosages based, at least in part, on blood glucose readings. Such insulin pump systems have been designed to additionally interface with a controller device that can receive blood glucose readings from the CGM and/or BGM devices, and can determine and direct the insulin infusion pumps to deliver insulin at appropriate dosages. Such controllers have included, for example, smartphones that are programmed to communicate wirelessly with CGM and BGM devices, and to communicate wirelessly with insulin infusion pumps.

SUMMARY

Systems, devices, and methods provided herein provide can network topologies for insulin pump systems through which a durable controller device is able to securely communicate with a mobile computing device (e.g., smartphone) and various peripheral devices (e.g., BGM, COM, smart pens) using a common wireless communication standard, such as BLUETOOTH low energy (BLE). Such durable controllers can be part of insulin delivery systems that also include insulin pumps. Durable controllers can be programmed to determine and modulate dosages for patients based on blood glucose readings from BGMs and CGMs, and can direct insulin pumps to deliver insulin dosages based on the determinations. The durable controllers can be physically connected to insulin pump devices, which may be disposable and replaceable over time. Durable controllers can manage the delivery of insulin locally, including making dosing determinations, dosing adjustments, storing and processing patient data (e.g., blood glucose readings) in real time, and controlling operation of the insulin pump. Examples of such controllers, mobile computing devices, and peripheral devices, and the interactions between them, are described in Appendix A, which is incorporated herein by reference.

Durable controllers can be a hub of communication with multiple different devices, such as with peripheral devices (e.g., BGM, CGM, smart pens) that provide real time patient data used by the durable controllers for dosing determinations, mobile computing devices (e.g., smartphones, tablets, wearable computing devices) that receive data (e.g., patient data, dosing data) from durable controllers and provide updated patient dosing models to the durable controllers, and/or other devices. Such communication can be provided by durable controllers concurrently between multiple different devices using the same wireless communication chipset and interface, such as a BLE chipset and communications interface. Various techniques can be used to facilitate concurrent communication using the same chipset and interface on durable controllers, such as connecting to peripheral device one at a time to obtain new patient data, syncing states between the durable controller and the mobile computing device (and a mobile application running thereon) when a connection is reestablished there between, having the durable controller act in a "central role" in communication with peripheral devices and in a "peripheral role" in communication with mobile computing devices, and/or other techniques to ensure data integrity and proper device operation.

In one implementation, an insulin delivery system using an on-body network of devices includes an insulin delivery device that is adapted to administer dosages of insulin to a patient; a controller that is adapted to control operation of the insulin delivery device, to establish a first network connection in which the controller acts in a central role, and to establish a second network connection in which the controller acts in a peripheral role; one or more peripheral devices that are adapted to generate patient data related to blood glucose levels and to transmit the patient data wirelessly over the first network connection, the peripheral devices acting in a peripheral role over the first network connection; and a mobile application installed on a mobile computing device that is programmed to communicate with the controller over the second network connection, the mobile application communicating in a central role over the second network connection.

Certain implementations can include one or more of the following features. The first network connection can be a first BLUETOOTH low energy (BLE) connection. The second network connection can be a second BLE connection. The controller can include a single BLE chipset and interface over which the first BLE connection and the second BLE connection are provided. Additionally or alternatively, the controller can include multiple BLE chipsets and interfaces (e.g., 2, 3, or 4) with each chipset configured to facilitate one or more BLE connections. For example, a first BLE connection can be provided by a first chipset while a second BLE connection is provided by a second chipset.

Certain implementations can include one or more advantages. For example, by using a single chipset and interface to communicate both with peripheral devices (e.g., BUM, CGM) and mobile computing devices, durable controllers can be manufactured less expensively and can also enable low energy communication (e.g., BLE) to be used across all devices, which can minimize power consumption and increase battery life. Additionally, use of a single chipset and interface to communicate both with peripheral devices (e.g., BGM, CGM) and mobile computing devices can allow for a more compact structure for the controller that allows for easier use by patients. Being as insulin controllers are generally used round the clock, ease of use and reduced size/weight contribute significantly to the ability of patients to effectively and efficiently use such devices over time. In another example, techniques for providing concurrent communication between durable controllers and both peripheral devices and mobile computing devices can ensure data integrity, security, and command sequence continuity among the devices.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings may indicate like elements.

DETAILED DESCRIPTION OF ILLUSTRATIVE EMBODIMENTS

Figure 1:
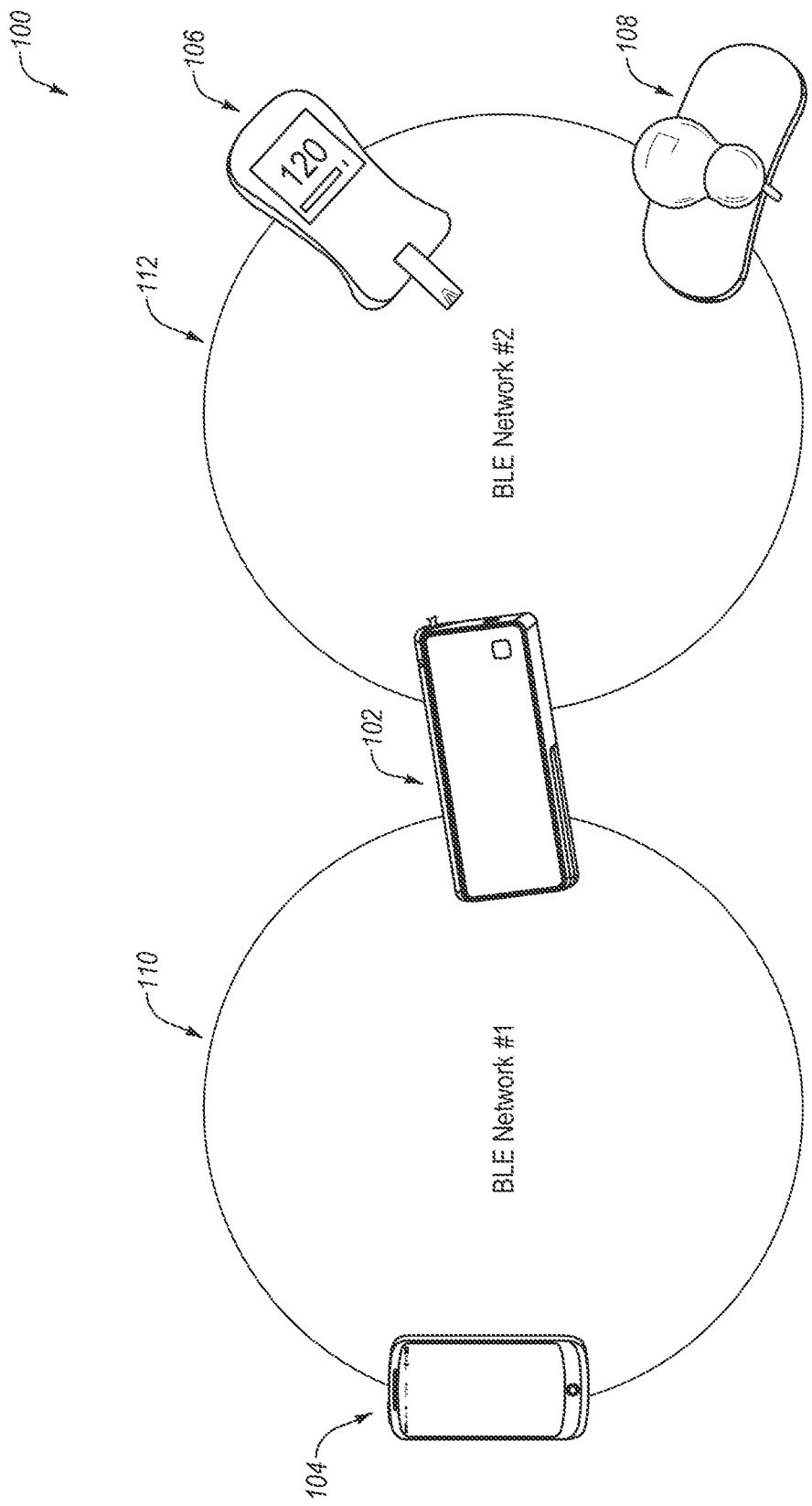
FIG. 1 depicts a network topology for an example on-body network.

FIG. 1 depicts a network topology for an example on-body network 100 that includes a durable controller 102, a mobile computing device 104 that is running a mobile application, a BGM 106, and a CGM 108.

The durable controller 102 can be part of an insulin delivery system that includes an insulin pump, which can dispense insulin under the direction of the controller 102. The controller 102 can act as the central hub of the on-body wireless network 100, and can interface with two separate BLE networks 110 and 112 that are used to communicate with the mobile device 104 and the peripheral devices 106/108, respectively. The durable controller 102 includes memory storage and one or more processors for storing computer instructions and executing those instructions, respectively. The memory of the durable controller 102 can additionally store information on use of the insulin delivery system or parameters and settings associated with the insulin delivery system and/or the patient using the insulin delivery system.

The mobile computing device 104 can be any of a variety of appropriate mobile computing devices, such as a smartphone, a tablet computing device, wearable computing devices, lap top computers, personal digital assistants, and/or other mobile computing devices capable of wireless communication with the durable controller 102. The mobile computing device 104 includes memory for storing data and computer instructions, one or more processors for executing computer instructions, and a user interface for accepting user input and providing output (e.g., visual, audio, tactile) to the user. The mobile computing device 104 can have a mobile application installed and running on it that is programmed to securely pair and communicate with the durable controller 102 through the BLE network 110.

In the BLE network 110, the controller 102 can assume a "peripheral role" and the mobile computing device 104 can assume a "central role." For example, the controller 102 advertise its presence through periodically transmitted beacon signals, which the mobile computing device 104 can detect and use to establish the BLE network 110. In some implementations, the controller 102 can connect with one mobile computing device (e.g., the mobile computing device 104) at a time over the BLE network 110. The controller 102 and the mobile computing device 104 can be programmed to attempt to maintain a consistent and persistent connection over the BLE network 110, when possible (e.g., when the controller 102 and the mobile computing device 104 are within range for communicating over BLE). Furthermore, by assuming a "central role," the mobile computing device 104 can help to preserve battery power and processing usage of the controller 102.

The BGM 106 and the CGM 108 can be peripherals that are approved/verified/certified for connection with the controller 102. The BGM 106 and the COM 108 can be configured to be securely paired with the controller 102, which may be performed by the controller 102 alone or in combination with communication with the mobile computing device 104 (and a remote server system that is programmed to verify/validate peripheral devices). For example, the controller 102 as well as the peripherals (e.g., BGM 106, CGM 108) can maintain whitelists of approved/verified devices for pairing, which can be established and verified through communication with a remote server system or other remote computing device/system via the mobile computing device 104 (which can act as a gateway for the controller 102 to the remote server system). For example, the controller 102 can maintain a whitelist that includes the BGM 106, the CGM 108, and the mobile computing device 104 as approved devices with which the controller 102 is approved to communicate with over one or more BLE networks. As another example, the BGM 106 and the CGM 108 can maintain whitelists that identify the controller 102 and/or the mobile computing device 104 as approved devices for communication over one or more BLE networks.

In some implementations, in the BLE network 112, the controller 102 assumes a "central role." and the peripheral devices (e.g., CGM 108, BGM 106) can assume a "peripheral role." For example, the BGM 106 and the CGM 108 can advertise their presence through periodically transmitted beacon signals, which the controller 102 can detect and use to establish the BLE network 112. The controller 102 may connect to multiple different peripherals, such as connecting to one active CGM, multiple active CGMs, multiple BGMs, a smart pen (not depicted), and/or other peripheral devices that may be part of the on-body network 100. These connections by the controller 102 to multiple different peripheral devices can be over a single network (such as BLE network 112) or over multiple communications networks. In some implementations, the multiple different networks used by the controller 102 to communicate with various peripheral devices can utilize different wireless communications protocols. For example, the controller 102 can establish the BLE network 112 to communicate with the CGM 108 and BGM 106 while establishing a second network to communicate with additional peripheral devices (e.g., additional CGMs, BGMs, smart pens, etc.) using a second wireless communication protocol such as Near Field Communication (NFC), radio frequency (RF) communication, Wifi, or another wireless communication protocol. Continuing with this example, the controller 102 can establish a third network using NFC to communicate with a smart pen (e.g., an insulin or glucagon pen).

As mentioned above, the BGM 106 and the CGM 108 can maintain whitelists of paired centrals, such as the controller 102. However, the BGM 106 and the CGM 108 may only connect to one central at a time. As described below with regard to FIG. 3, the controller 102 can use the same BLE chipset and interface for communicating over the BLE networks 110 and 112, and as a result, can connect to a single peripheral device at a time over the BLE network 112 by periodically connecting to peripheral devices (e.g., BGM 106, CGM 108) one at a time, obtaining data from the connected device, disconnecting, and then establishing a connection with other ones of the peripheral devices. Given limited data storage capacity on peripheral devices and the improved performance of the controller 102 in determining appropriate insulin dosing with real time (or near real time) patient information (e.g., blood glucose readings), such individual connections with peripheral devices may be established in a timely manner (e.g., every few seconds, every minute, every 5 minutes) to guarantee that timely data is updated to and used by the controller 102.

Although not depicted, other peripheral devices are also possible as part of the on-body network 100, such as smart pens that will also communicate over the BLE network 112. Additionally, the on-body network 100 can include multiple BGMs, multiple CGMs, and/or multiple other peripheral devices that are able to communicate with the controller 102 over the BLE network 112.

In some implementations, the controller 102 is configured to communicate with each peripheral device using multiple communications protocols. For example, the BGM 106 can include an NFC tag that can communicate BLE pairing information to the controller 102 using NFC. The controller 102 includes a NFC chipset for detecting the NFC communications from the BGM 106. The controller 102 receives the BLE pairing information for the BGM 106 via the NFC communication and uses this information to establish the BLE network 112 for communicating with the BGM 106. This example also applies to the CGM 108 and other peripheral devices such as smart pens. As another example, the COM 108 can include an RFID tag that can communicate BLE pairing information to the controller 102. The controller 102 can include an RFID tag reader to read the pairing information from the RFID tag. The controller 102 can then use the received BLE pairing information to establish the BLE network 112 for communication with the CGM 108. This example also applies to the BGM 106 and other peripheral devices such as smart pens.

Figure 2:
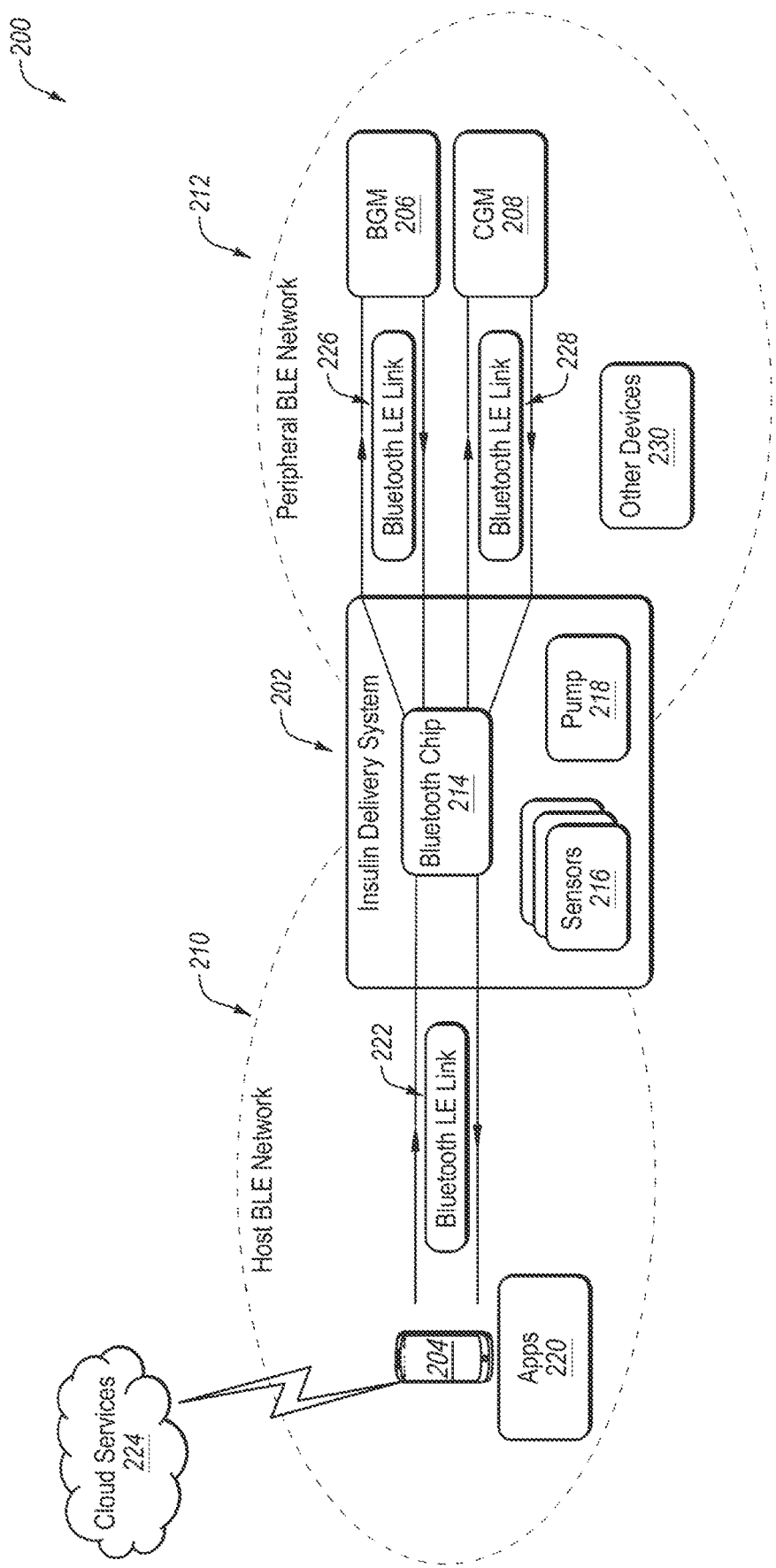
FIG. 2 depicts a network topology for an example on-body network.

FIG. 2 depicts a network topology for an example system 200 that includes an insulin delivery system 202 (IDS 202), a mobile computing device 204 that is running a mobile application 220, a BGM 206, a CGM 208, another peripheral device 230, and a remote computer system providing cloud services 224.

The IDS 202 can be similar to the durable controller 102, the mobile computing device 204 can be similar to the mobile computing device 104, the BGM 206 can be similar to the BGM 106, and the CGM 208 can be similar to the CGM 108. The IDS 202 can communicate with the mobile computing device 204 and the mobile application 220 over a host BLE network 210 in which the mobile device 204/mobile application 220 act as a central and the IDS 202 acts as a peripheral. For example, the IDS 202 and the mobile device 204/mobile application 220 can establish a BLUETOOTH LE link 222, over which requests, responses, alarms, data, and other information are transmitted between the IDS 202 and the mobile device 204/mobile application 220. The host BLE network 210 can be similar to the BLE network 110. As discussed with respect to FIG. 1 above, other wireless communications protocols can be used in place of or in addition to BLE to establish one or more of the networks. Additionally, as discussed above with respect to FIG. 1, the IDS 202 can communicate with each device using multiple communications protocols. For example, the IDS 202 can receive BLE pairing information from the CGM 208 using NFC.

The IDS 202 can communicate with the peripheral devices 206, 208, and 230 over a peripheral BLE network 212 in which the IDS 202 acts as a central and the peripheral devices 206, 208, and 230 act as peripherals. For example, the IDS 202 and the BGM 206 can establish a BLUETOOTH LE link 226, over which patient data and other information are transmitted to the IDS 202 from the BGM 206. Similarly, the IDS 202 and the CGM 208 can establish a BLUETOOTH LE link 228, over which patient data and other information are transmitted to the IDS 202 from the CGM 208. Although not depicted, similar communication links can be established between the IDS 202 and the other peripheral devices 230. The peripheral BLE network 212 can be similar to the BLE network 112.

The IDS 202 can include a single BLUETOOTH chipset and interface 214 over which the IDS 202 establishes and communicates over both of the networks 210 and 212. The IDS 202 can include a durable controller (similar to the controller 102) as well as an insulin pump 218 that is configured to deliver insulin in dosages determined and directed by the controller. The IDS 202 can additionally include one or more integrated sensors 216 that can be used by the controller to determine dosing information. The sensors 216 can include, for example, occlusion sensors, accelerometers, location sensors (e.g., home sensors), and/or other sensors).

The system 200 additionally includes a cloud service 224 that the mobile device communicates with over one or more network connections (e.g., mobile data networks, Wi-Fi networks, internet, and/or combinations thereof). The cloud service 224 can maintain a large and redundant data storage system that is capable of maintaining patient data over time, which can be used to generate accurate patient dosing models that are used by the IDS 202. Additionally, the IDS 202 can communicate patient treatment information to the cloud service 224.

Figure 3:
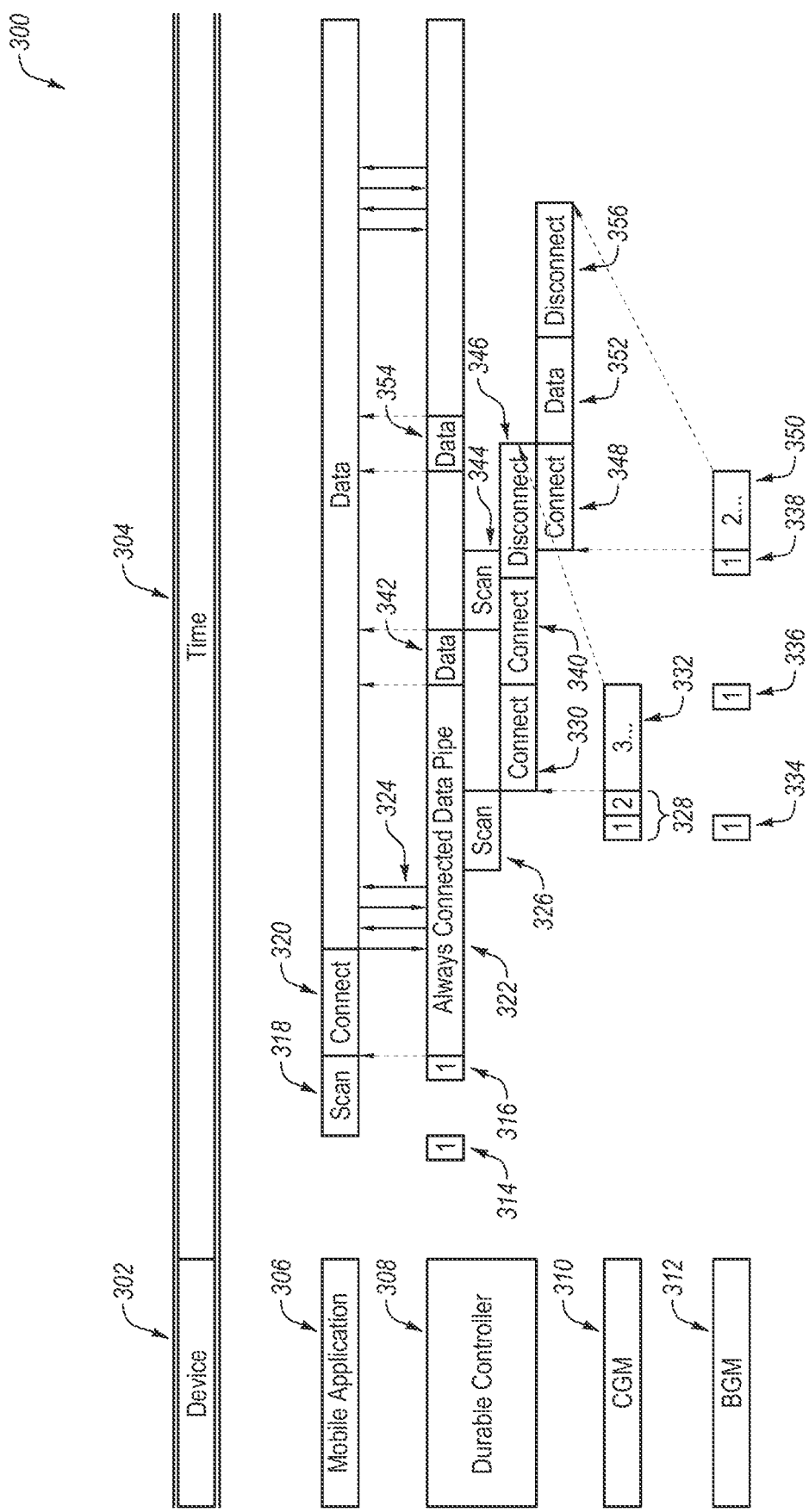
FIG. 3 is an example communication timeline for devices that are part of an example on-body network.

FIG. 3 is an example communication timeline 300 for devices 302 that are part of an example on-body network. The devices include a mobile application 306 (similar to the mobile application 220) that is running on a mobile computing device (similar to the mobile computing devices 104 and 204), a durable controller 308 (similar to the controller 102 and the IDS 202), a CGM 310 (similar to the CGM 108 and the CGM 208), and a BGM 312 (similar to the BGM 106 and the BGM 206). As described above, the network topology can be implemented on the durable controller 308 acting as a hub of the on-body network, and additionally can be implemented using a single network chipset (e.g., BLE chipset) and interface on the controller 308 (although implementations with the durable controller 308 having multiple network chipsets and interfaces are also possible). The on-body network for these devices 302 is depicted as being established over the timeframe 304, which represents actions by and communication between the devices 302, and is not necessarily to scale.

The timeline 300 can begin with the durable controller 308 and the mobile application 306 establishing a connection (e.g., BLE network 110, 210) with each other in which the controller 308 acts as a peripheral and the mobile application 306 acts as a central. For example, the durable controller 308 can advertise its presence through periodic beacon signals 314 and 316, which the mobile application 306 can detect when intermittently scanning 318 for the controller 308. The mobile application 306 and the controller 308 can have previously been securely paired and authenticated, for example, through authentication with a remote computer system, such as the cloud services 224. As a result, the mobile application 306 can be programmed to scan specifically for the durable controller 308, such as through a unique identifier (e.g., security key, network identifier) for the controller 308. Once detected, the mobile application 306 can connect 320 with the durable controller 308, such as through performing a secure BLE pairing process during which shared secrets are used to verify and authenticate both ends of the connection. Once connected, the durable controller 308 and the mobile application 306 can maintain an always-connected data pipe 322, as indicated by the example network traffic 324. For example, the mobile application 306 can provide requests to the controller 308 (e.g., initiate bolus), which the controller 308 can acknowledge receipt of via a response, perform, and verify that performance has been completed in another response to the mobile application 306. This communication can be an example BLE network connection, such as the example networks 110 and 210 described above with regard to FIGS. 1 and 2, respectively.

While connected to the mobile application 306, the durable controller 308 can additionally establish network connections with peripheral devices, such as the CGM 310 and the BGM 312. Unlike the connection with the mobile application 306, the connection with the peripheral devices can be established by the controller 308 acting as a central (as opposed to acting as a peripheral in the communication with the mobile application 306) and the peripherals 310, 312 can act as peripherals. For example, the CGM 310 and the BGM 312 can both advertise their presence though periodic beacon signals 328 (for the CGM 310) and signals 334, 336, 338 (for the BGM 312). These example beacon signals can be of different durations (e.g., the example beacon signal 328 has longer duration (e.g., two seconds) whereas the beacon signals 334, 336, and 338 have a shorter duration (e.g., one second)) and can also occur over different time intervals. For example, the BGM 312 can broadcast every five seconds, whereas the CGM 310 may broadcast at longer intervals of time (e.g., every ten seconds, every minute, every five minutes).

The controller 308 can be programmed to establish a connection with one peripheral device as a time. For example, the controller 308 scans 326 and, although both the CGM 310 and the BGM 312 are broadcasting at that time the scanning 326 is being performed, may pick up only one of these peripherals for the network connection (e.g., BLE network 112, BLE network 212). For example, the durable controller 308 can connect 330 with the CGM 310, which can cause the CGM 310 to transmit 332 patient data (e.g., timestamped blood glucose readings) that is received 340 by the controller 308. The controller 308 can process the data, use it to inform current and future dosing for the patient, and can transmit 342 the data to the mobile application 306, which may store the data, perform additional processing on the data, and/or relay the data to a remote computer system for further processing, storage, and analysis (e.g., refinement of patient dosing model used by the application 306 and/or the controller 308). Once the controller 308 has received the data 340, the controller 308 can disconnect 346 from the CGM 310 and can initiate a scan 344 for other peripheral devices. In this example, the scan 344 picks up the beacon signal 338 from the BGM 312, which prompts the controller 308 to initiate the connection 348 with the BGM 312. The BGM 312 can then transmit 350 patient data to the controller 308, which can receive the data 352 and perform similar processing, analysis, and dosing based on the data 352 as with the data from the CGM 310. This data can additionally be transmitted 354 by the controller 308 to the mobile application 306, which can use and/or retransmit the data similar to the CGM data. Once the data has been received, the controller 308 can disconnect 356 from the BGM 312. The controller 308 can repeatedly connect and disconnect with the peripheral devices 310, 312 one at a time, and may toggle between connections with the peripheral devices 310, 312 at sufficient increments of time so that the controller 308 receives recent patient data (e.g., data generated no longer than 30 seconds prior, 1 minute prior, 5 minutes prior to being transferred to the controller 308). For example, the controller 308 can rotate through connections with all available and authorized peripheral devices.

In contrast with the connections with the peripheral devices, which are initiated and dropped at various intervals, the durable controller 308 can work to maintain a persistent connection with the mobile application 306. However, this connection with the mobile application 306 may drop off at various points in time, such as the mobile application 306 being powered off, the mobile application 306 being out of range of the controller 308, and/or other communications over a common network chipset/interface (e.g., single BLE chipset) causing the communication with the mobile application 306 to be temporarily suspended or paused. In such situations, when a connection between the controller 308 and the mobile application 306 is reestablished, the controller 308 and the mobile application 306 can sync their states before performing additional operations. For example, if the mobile application 306 sends a command to the controller 308 to administer a bolus and then the connection between the application 306 and the controller 308 falls off, the controller 308 can continue to administer the bolus but will not be able to provide confirmation to the mobile application 306 that the bolus has been provided. When the connection is reestablished, the controller 308 and the mobile application 306 can sync their states, which can prevent the mobile application 306 from providing another command to administer the bolus dose and the controller 308 from administering a second, potentially dangerous bolus when only one was requested.

Figure 4:
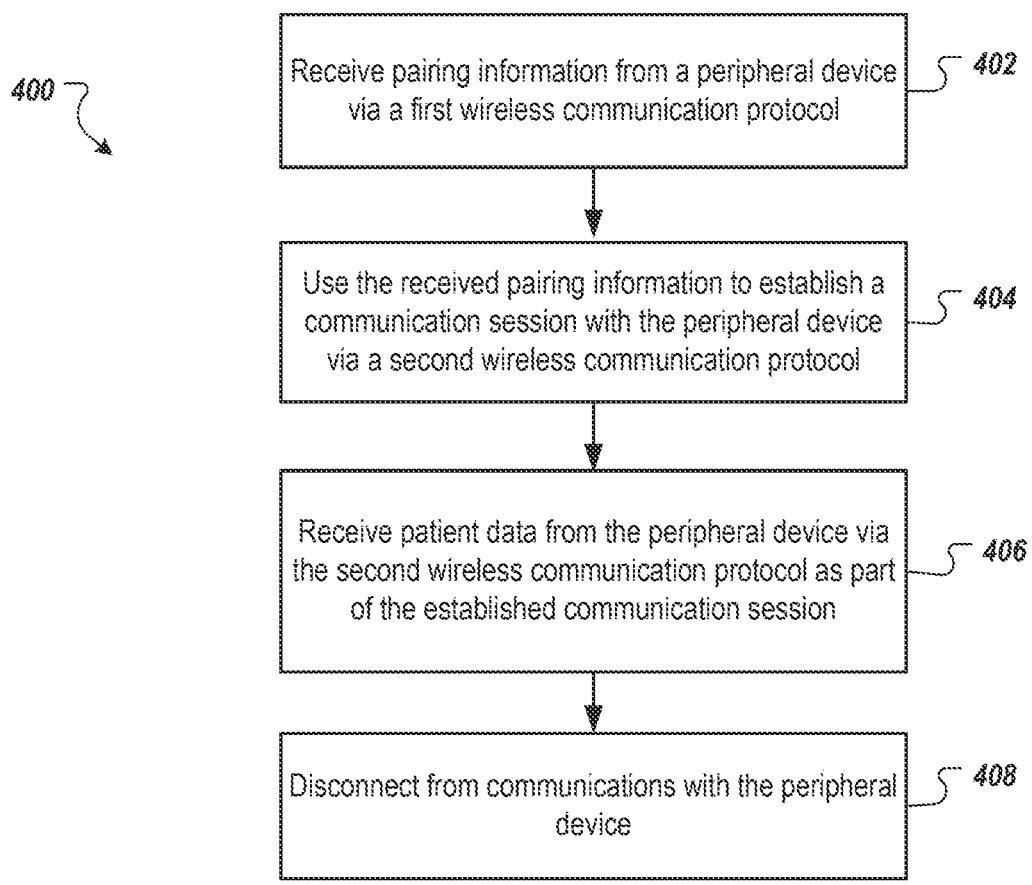
FIG. 4 is a flow chart of a process for communicating between a controller and a peripheral device.

FIG. 4 shows a flow chart of a process 400 for communicating between a controller and a peripheral device. The process 400 can be performed, for example, by the durable controller 102 of FIG. 1, the insulin delivery system 202 of FIG. 2, the durable controller 308 of FIG. 3, or a similar device.

The process 400 includes receiving pairing information from a peripheral device via a first wireless communication protocol (402). For example, the durable controller 102 receives pairing information from CGM 108 via near field communication (NFC). For example, the CGM 108 can include an NFC tag that includes BLE pairing information for the CGM 108. The durable controller 102 can include an NFC reader that an receive the NFC communication from the NFC tag and extract the BLE pairing information from the NFC communication.

The process 400 further includes using the received pairing information to establish a communication session with the peripheral device via a second wireless communication protocol (404). For example, the durable controller 102 can use the received BLE pairing information to establish a BLE communication session with the CGM 108 (such as, for example, the BLE network 112 of FIG. 1).

The process 400 further includes receiving patient data from the peripheral device via the second wireless communication protocol as part of the established communication session (406). For example, the durable controller 102 can receive time stamped blood glucose information for a patient from the CGM 108 via the BLE communication session (e.g., the BLE network 112).

The process 400 optionally includes disconnecting from communications with the peripheral device (408). For example, the controller 102 can end the communication session with CGM 108 once the patient information has been received. This can free up the controller 102 to establish communications sessions with additional peripheral devices, such as the BGM 106, a smart pen, or another peripheral device.

A number of embodiments of the invention have been described. Nevertheless, it will be understood that various modifications may be made without departing from the spirit and scope of the invention. Accordingly, other embodiments are within the scope of the following claims.

What is claimed is:

1. A controller in an insulin delivery system for the delivery of insulin to a patient, the controller configured to control operation of an insulin delivery device, the controller comprising: chipset for establishing communications with a glucose monitor and a smartphone; one or more processors; and computer memory storing instructions that, when executed by the one or more processors, cause the one or more processors to: establish, using the chipset, a first network connection with the glucose monitor; establish, using the chipset, a second network connection with the smartphone, the smartphone running a mobile application, wherein the mobile application is executed by the smartphone; receive, via the first network connection, patient data related to blood glucose levels from the glucose monitor; transmit, via the second network connection, the patient data related to blood glucose levels to the smartphone; receive, from the smartphone via the second network connection, an instruction to administer an insulin dosage, wherein the instruction to administer the insulin dosage is initiated by the mobile application running on the smartphone, and wherein the insulin dosage is based at least in part on the patient data related to blood glucose levels transmitted to the smartphone; and transmit, to the smartphone via the second network connection, a communication verifying that the administration of the insulin dosage has been completed.

2. The controller of claim 1, wherein the one or more processors are further operable to:
receive, via the second network connection, operating instructions from the smartphone; and
operate the insulin delivery device according to the operating instructions received from the smartphone.

3. The controller of claim 1, wherein:
in the first network connection with the glucose monitor, the controller is configured to assume a central role and the glucose monitor is configured to assume a peripheral role, and in the second network connection, the controller is configured to assume the peripheral role and the smartphone is configured to assume the central role.

4. The controller of claim 1, wherein the one or more processors are operable to synchronize a state of the controller with a state of the smartphone in response to the second network connection with the smartphone being interrupted and subsequently reestablished.

5. The controller of claim 1, wherein the one or more processors are operable to receive the patient data related to the blood glucose levels from the glucose monitor via broadcast signals transmitted at an interval of every five minutes.

6. The controller of claim 1, wherein the smartphone communicates with a cloud service.

7. The controller of claim 1, wherein the one or more processors are further operable to process the patient data related to blood glucose levels received from the glucose monitor to inform future insulin dosing to the patient.

8. A method to be performed by a controller of an insulin delivery system for the delivery of insulin to a patient, the method comprising the steps of:
establishing, using a chipset, a first network connection with a glucose monitor;
establishing, using the chipset, a second network connection with a smartphone executing a mobile application;
receiving, via the first network connection, patient data related to blood glucose levels from the glucose monitor;
transmitting, via the second network connection, the patient data related to blood glucose levels to the smartphone;
receiving, from the smartphone via the second network connection, an instruction to administer an insulin dosage, wherein the instruction to administer the insulin dosage is initiated by the mobile application running on the smartphone, and wherein the insulin dosage is based at least in part on the patient data transmitted to the smartphone; and
transmitting, to the smartphone via the second network connection, a communication verifying that the administration of the insulin dosage has been completed.

9. The method of claim 8, further comprising the steps of:
receiving, via the second network connection, operating instructions from the smartphone; and
operating an insulin delivery device according to the operating instructions received from the smartphone.

10. The method of claim 8, wherein:
in the first network connection, the controller is configured to assume a central role and the glucose monitor is configured to assume a peripheral role; and
in the second network connection, the controller is configured to assume the peripheral role and the smartphone is configured to assume the central role.

11. The method of claim 8, wherein receiving the patient data related to blood glucose levels comprises receiving time stamped blood glucose information from a continuous glucose monitor.

12. The method of claim 8, wherein the first and second network connections are established using a first wireless communication protocol.

13. The method of claim 8, the method further comprising the step of:
receiving, from the glucose monitor via a second wireless communication protocol, pairing information for establishing the first network connection, the second wireless communication protocol being different from the first wireless communication protocol, wherein establishing the first network connection with the glucose monitor includes using the pairing information to establish the first network connection with the glucose monitor.

14. The method of claim 8, wherein, when receiving, via the first network connection, patient data related to blood glucose levels from the glucose monitor, further comprises:
receiving broadcast signals from the glucose monitor at an interval of every five minutes.

15. The method of claim 8, further comprises:
communicating via the smartphone with a cloud service.

16. The method of claim 8, further comprising the step of:
processing the patient data related to blood glucose levels received from the glucose monitor to inform the patient of future insulin dosing.

\* \* \* \* \*